United States Patent [19]

Fonger et al.

[11] Patent Number: 5,354,276
[45] Date of Patent: Oct. 11, 1994

[54] INTERNAL MAMMARY ARTERY CATHETER AND METHOD

[75] Inventors: James D. Fonger, Wayland, Mass.; Mark P. Ashby, Laguna Niguel, Calif.

[73] Assignee: Applied Medical Resources Corporation, Laguna Hills, Calif.

[21] Appl. No.: 32,375

[22] Filed: Mar. 18, 1993

[51] Int. Cl.⁵ .......................................... A61M 29/00
[52] U.S. Cl. ..................... 604/96; 604/104; 606/191; 606/192; 606/194
[58] Field of Search ................ 120/658, 772; 606/191, 606/192, 193, 194; 604/93, 95, 96, 97, 99, 103, 104

[56] References Cited

U.S. PATENT DOCUMENTS

| | | |
|---|---|---|
| 4,311,133 | 1/1982 | Robinson . |
| 4,315,512 | 2/1982 | Fogarty ................................ 604/97 |
| 4,444,188 | 4/1984 | Bazell . |
| 4,552,127 | 11/1985 | Schiff ................................ 606/192 |
| 4,564,014 | 1/1986 | Fogarty . |
| 4,614,188 | 9/1986 | Bazell . |
| 4,820,283 | 4/1989 | Schickling . |
| 4,909,258 | 3/1990 | Kuntz . |
| 4,968,300 | 11/1990 | Moutafis . |
| 5,087,246 | 2/1992 | Smith . |

OTHER PUBLICATIONS

"An Improved Technique for Internal Mammary Artery Graft Preparation"; by Thomas J. Fogarity, M.D. et al.

Primary Examiner—C. Fred Rosenbaum
Assistant Examiner—N. Kent Gring
Attorney, Agent, or Firm—Richard L. Myers

[57] ABSTRACT

A catheter includes a hub and a stylet extending through the hub to a distal end of the catheter. A balloon fixed at its proximal end to the hub and at its distal end to the stylet is axially extendible by operation of the stylet. Inserting the catheter, in its extended state, into an arterial conduit enables the balloon to be inflated and to exert only radial forces against the interior of the vessel. This apparatus and procedure overcomes spasms normally associated with preparation of an arterial conduit, such as the internal mammary artery, for bypass surgery. Extension of the balloon to as much as six times its initial length can be accomplished by positioning a separation spring between the stylet and the balloon.

8 Claims, 4 Drawing Sheets

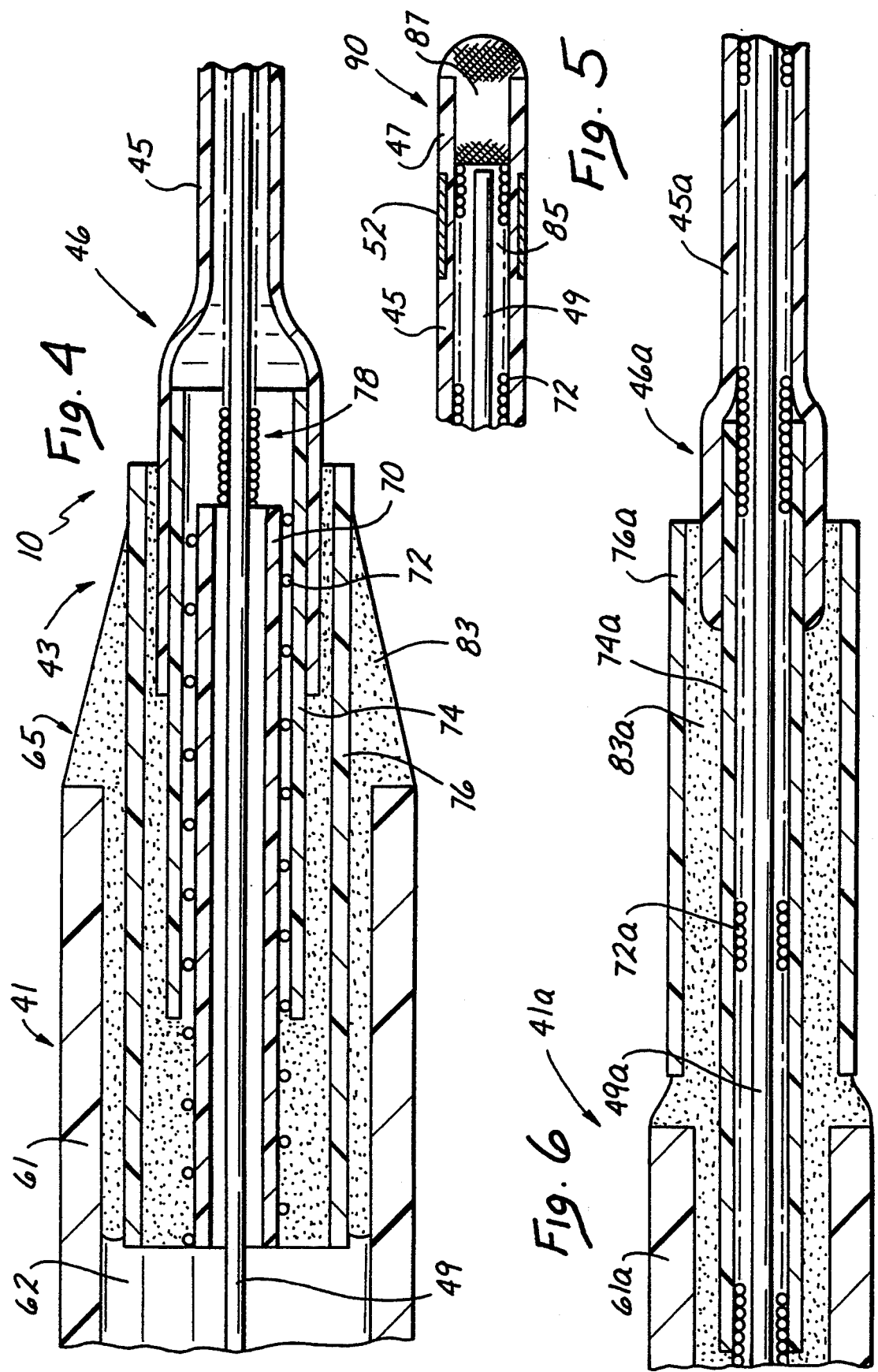

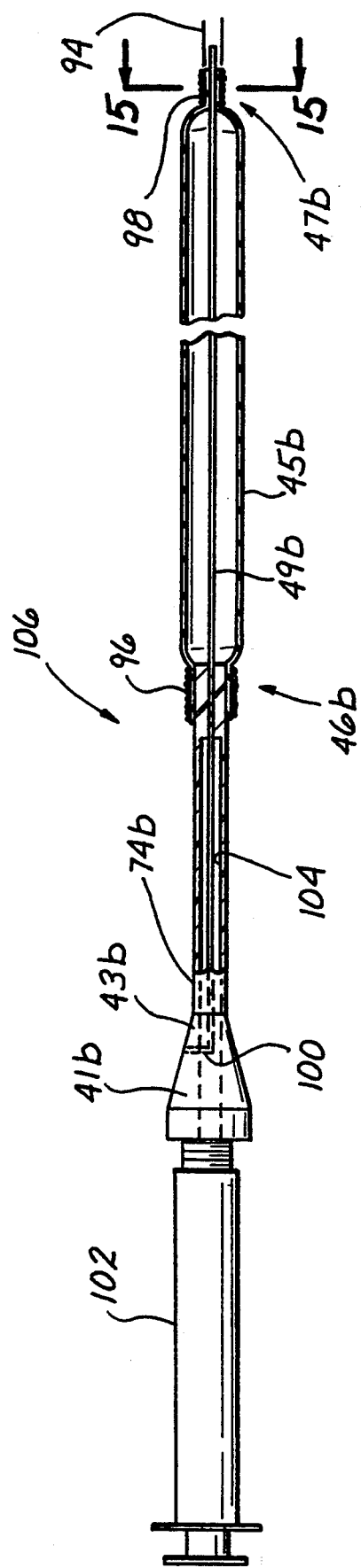
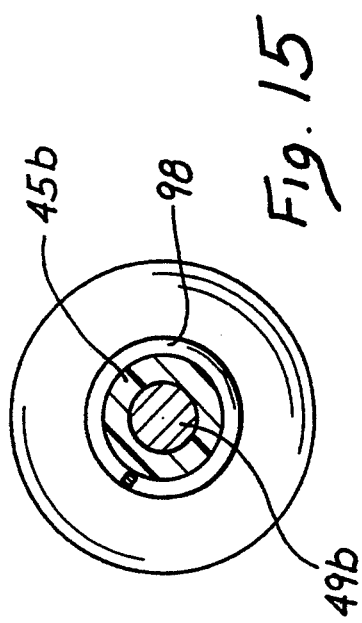
Fig. 14
Fig. 15

INTERNAL MAMMARY ARTERY CATHETER AND METHOD

BACKGROUND OF THE INVENTION

1. Field of the Invention

This invention relates generally to an apparatus for preparing autologous vessels for use in bypass surgery and more specifically to a catheter and method for dilating the internal mammary artery or other arterial conduits for such use.

2. Discussion of the Prior Art

Internal mammary arteries are vessels which originate at the subclavian arteries and deliver blood to the sternum and musculature of the chest wall. These arteries along with gastroepiploic and inferior epigastric arteries, are being used increasingly in cardiovascular bypass surgery.

It is the purpose of a bypass operations to provide a passage from a site of free flowing blood to a site distal to an occlusion in a coronary artery. In the past, saphenous veins have been harvested from the legs of patients and grafted to the coronary arteries for this purpose. One end of the graft has been attached to the aorta which provides the source of the blood, while the other end of the graft has been attached to the coronary artery distal of the occlusion. In this manner, blood from the aorta has bypassed the occlusion to feed the heart muscle.

The internal mammary artery (IMA) is the most frequently used arterial conduit for bypass grafting. In harvesting the IMA from the chest wall, the endothoracic facia is sometimes incised from around the IMA to sever the constricting bands of circumferential fascia. While the IMA remains attached to the subclavian artery, the mobilized end of the IMA pedicle is attached to the coronary artery. An obvious advantage over use of the saphenous vein is the fact that only one end of the IMA pedicle needs to be reattached while the other end can remain in its natural position.

Unfortunately, the IMA has characteristics which cause it to spasm or constrict in response to the trauma associated with mobilization. It has been found that mechanical circumferential stretching of the IMA tends to overcome this spasm leaving a relaxed, larger diameter conduit for bypass surgery.

In the past the stretching of the IMA to overcome spasm has been accomplished by introducing a balloon catheter into the IMA and then drawing the catheter and the inflated balloon through the entire length of the artery. While this has tended to overcome the spasm, it has also resulted in denudation or stripping of the arterial intimal cell layer, sometimes referred to as the intima. This internal layer comprises important endothelial cells which line the interior of the IMA and allow the IMA to regulate its own diameter. For this reason, it is desirable to overcome the spasm without injuring or removing the intimal cell layer.

Procedures in the past have employed shear force gauges which measure the tensile force applied to the balloon catheter as the balloon is drawn through the IMA. While shear forces have been limited to approximately 30 grams, the intima is consistently damaged to an extent that has made this procedure clinically undesirable, and possibly damaging to the long term performance of the graft in the patient.

SUMMARY OF THE INVENTION

In accordance with the present invention, a catheter is provided with a housing and a stylet extending through the housing to a distal end of the catheter. An elastomeric balloon is attached to the wire at a distal end of the catheter and attached to the housing at a proximal end of the catheter. This balloon may have an initial length of only one inch. However, as the stylet is moved distally, the balloon stretches axially to a length as great as six inches in one case. In this process, the axial stretching of the balloon causes it to neck down thereby facilitating insertion of the catheter into the IMA. Once the balloon is in place, it can be inflated to exert a radial pressure against the walls of the IMA. It has been found that this radial force, devoid of any shear force, is sufficient to overcome the spasm of the IMA and yet preserve the intimal cell layer.

When the IMA has been suitably stretched, the balloon can be deflated. Even though the balloon is deflated it remains axially stretched so that it maintains a reduced radial dimension. In this state, the diameter of the catheter and the balloon is Less than the diameter of the IMA so the catheter can be retracted without exerting any shear force on the intima of the IMA.

In this procedure it is of particular advantage if the stylet is carried in a spring. In the absence of a spring, the stretched balloon may tend to grip the stylet preventing its further distal movement. This spring thus provides means for separating the stylet from the balloon to permit relative movement between the two as the stylet is inserted and the balloon is stretched axially.

In a particular embodiment of the invention, the balloon is formed from a material which can be sterilized in its extended elongate configuration without deleteriously affecting its elastomeric properties. In the manufacture of this catheter, the balloon can be fully stretched to its elongate configuration and the stylet fixed to the hub prior to sterilization. Thus, the catheter can be provided to the surgeon fully sterilized with the balloon in this elongated configuration. The method of using this catheter is greatly simplified since the surgeon is not required to advance the stylet or otherwise extend the balloon prior to use.

These and other features and advantages of the invention will be more apparent with the discussion of preferred embodiments and reference to the associated drawings.

DESCRIPTION OF THE DRAWINGS

FIG. 4 is an axial cross-section view of one embodiment of a hub associated with the catheter of the present invention.

FIG. 5 is an axial cross-section view of the distal tip of the catheter of FIG. 4;

FIG. 6 is an axial cross-section view of another embodiment of the hub assembly associated with the catheter of the present invention;

FIG. 7 illustrates the catheter and the IMA in spasm;

FIG. 8 illustrates the stylet deployed and the balloon axially stretched prior to insertion in the IMA;

FIG. 9 illustrates the catheter with stretched balloon inserted in the spasmed vessel;

FIG. 10 illustrates the balloon inflated to enlarge the vessel;

FIG. 11 illustrates the balloon deflated with the vessel maintaining its enlarged state;

FIG. 12 illustrates the catheter withdrawn from the enlarged vessel;

FIG. 13 illustrates the stylet retracted leaving the vessel in its enlarged state; and FIG. 14 is a side view partially in axial cross section of still a further embodiment of the catheter of the present invention; and FIG. 15 is a radial cross section view taken along the lines 15—15 of FIG. 14.

DESCRIPTION OF PREFERRED EMBODIMENTS AND BEST MODE OF THE INVENTION

Figure 1:
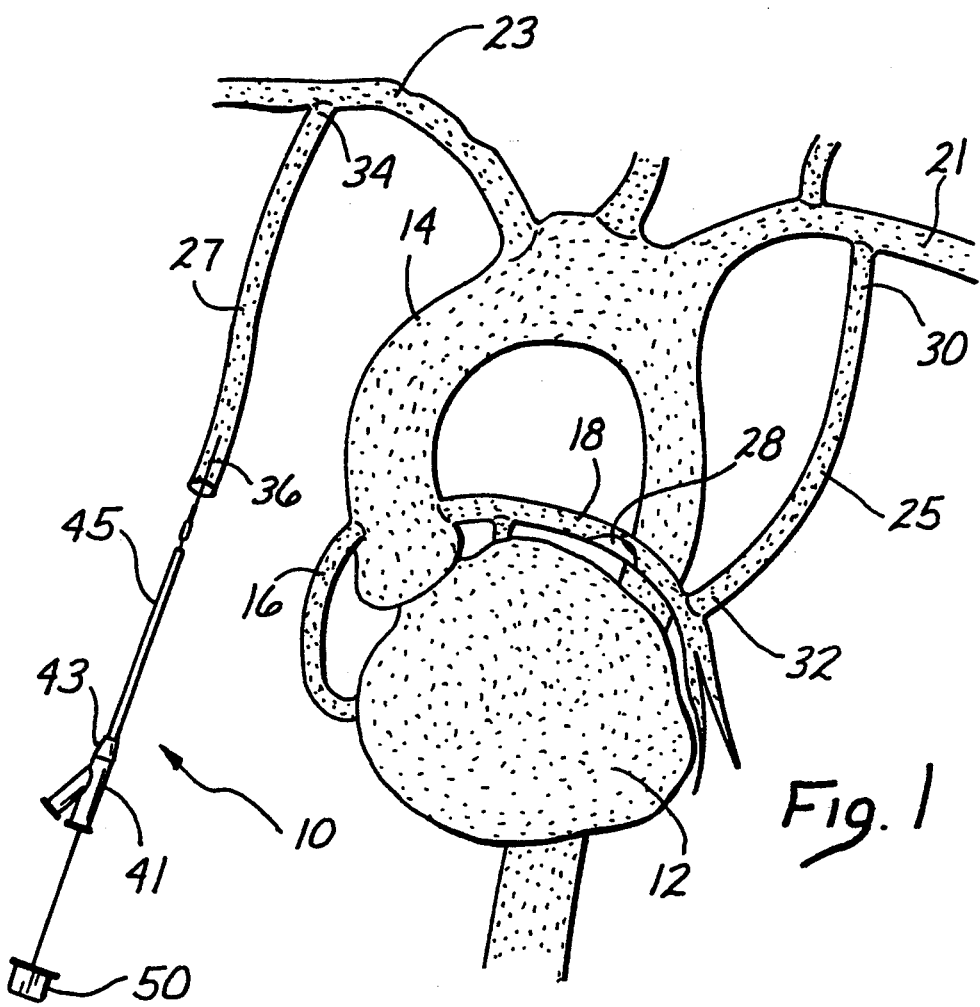
FIG. 1 is a schematic view of the heart and associated vasculature with an IMA catheter positioned to prepare the right IMA for coronary bypass surgery.

A catheter is illustrated in FIG. 1 and designated generally by the reference numeral 10. A heart 12 is also illustrated with a large arterial trunk, commonly referred to as the aorta 14, which conveys oxygenated blood to the entire circulatory system. As blood leaves the heart 12 and enters the aorta 14, it first encounters branches at a left coronary artery 16 and a right coronary artery 18. Subsequent branches form the aorta 14 include a left subclavian artery 21 and a right subclavian artery 23. Branching respectively from the subclavian arteries 21 and 23 are left and right internal mammary arteries respectively designated by the reference numerals 25 and 27. In the left internal mammary artery 25, the blood flows from a first end 30 to a second end 32. Similarly, in the right internal mammary artery 27 the blood flows from a first end 34 to a second end 36.

A coronary bypass operation is indicated when plaque formations in the coronary arteries, such as the arteries 16 and 18 block the flow of blood from the aorta 14 to distal regions of the heart. In the absence of oxygenated blood, the muscle of the heart 12 tends to deteriorate resulting in muyocardial infarction commonly referred to as a heart attack. The plaque material in the artery tends to form a stenosis 28 which partially and perhaps totally occludes the coronary artery 18. It is the purpose of a coronary bypass operation to feed fresh blood around the stenosis 28 to the distal portions of the coronary arteries. This aids in maintaining the muscle of the heart and thereby avoids further damage to the heart 12.

The internal mammary arteries 25 and 27 normally supply oxygenated blood to the musculature of the chest wall. As illustrated in FIG. 1, the second ends 32 and 36 of the respective arteries 25 and 27 have been mobilized or removed from this musculature thereby adapting the arteries 25 and 27 to function as grafts in a coronary bypass operation. In this context, the arteries are commonly referred to as Internal Mammary Artery Grafts or IMAs. In FIG. 1 the second end 32 of the left IMA has already been attached to the left coronary artery 18. The right coronary artery 27 is illustrated at a time following its mobilization from the chest wall but prior to its attachment to the right coronary artery 16.

The internal mammary arteries are particularly adapted for use in coronary bypass surgery since they are of sufficient length that their first ends 30 and 34 can be left attached to the associated subclavian arteries 21 and 23. Only the second ends 32 and 36 of the arteries 25 and 27 need be mobilized to complete the bypass. In comparison to prior methods requiring the harvesting of the saphenous vein, the use of the internal mammary arteries for bypass provides much reduced trauma to the patient.

Mobilization of arterial conduits causes these vessels to spasm due to the trauma of mobilization. It has been found that stretching the walls of the vessel 25 and 27 outwardly tends to relieve this spasm leaving the artery 25, 27 with a larger lumen increasing the probability of long term patency.

A device particularly adapted for relieving the spasm of the artery 27 is the catheter 10. This catheter includes a hub 41, a stress relief section 43, and a balloon 45. The balloon 45 has a proximal end 46 with a fixed relationship to the hub 41 and a distal end 47.

A stylet 49 extends from a Luer cap 50 through the hub 41 and the stress relief section 43 to engage the distal end 47 of the balloon 45. At this location, the balloon is preferably sealed around the stylet 49 by a thread 52.

Figure 2:
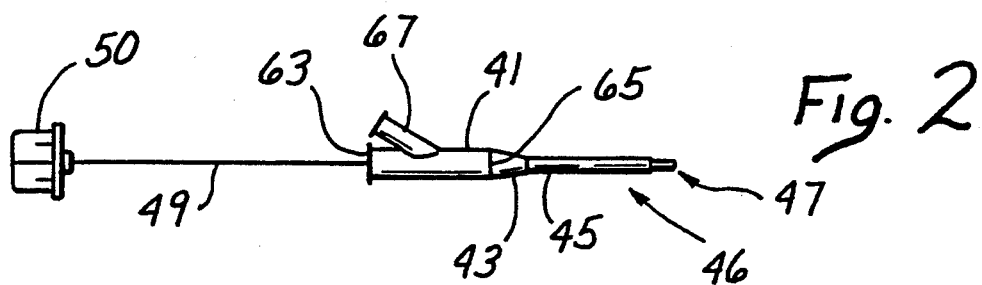
FIG. 2 is a side elevation view of the IMA catheter with the associated balloon in a natural, shortened state.
Figure 3:
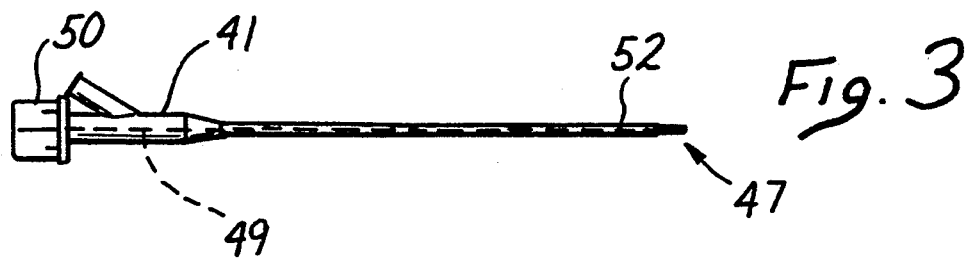
FIG. 3 is a side elevation view of the IMA catheter illustrated in FIG. 2 with the associated balloon in an axially elongated, radially contracted state.
Figure 7:
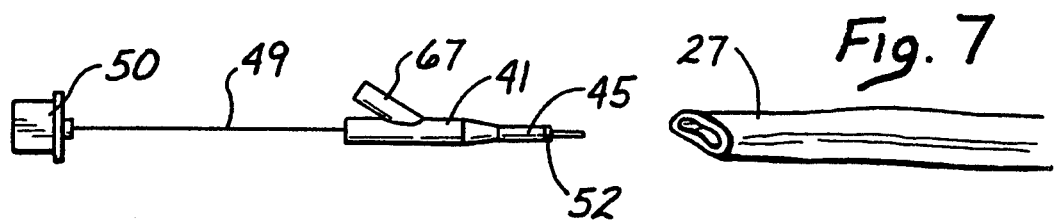
FIGS. 7-13 illustrate steps in a preferred method of the invention.

When the stylet 49 is advanced into the hub 41, the balloon 45 is stretched axially between the hub 41 and the distal end of the stylet 49. This stretches the balloon 45 from an axially compressed, radially expanded state illustrated in FIG. 2 to an axially stretched, radially contracted state as illustrated in FIG. 3. In the natural state, the balloon 45 may have a length such as 1.3 inches; in the expanded state, the balloon may have a length such as six inches.

The configuration of the catheter 10 can be better understood with reference to the cross-section views of FIGS. 4–6. In this embodiment, the hub comprises a standard "Y" hub having a housing or outer wall 61. This wall defines an interior cavity 62, an inlet port 63 at its proximal end, an outlet port 65 at its distal end, and a side port 67 best illustrated in FIG. 2.

The cavity 62 has a generally cylindrical configuration and the stylet 49 is disposed to extend along the axis of the cavity 62, into inlet port 63 and out of the exit port 65. Disposed concentrically outwardly of the stylet 49 at the exit port 65 are a spacer tube 70, a spring 72, a balloon support tube 74 and a stress relief tube 76.

In a process for manufacturing the catheter of FIG. 4, the stylet 49, tube 70, spring 72 and balloon support tube 74 are initially combined in a subassembly. The spacer tube 70 is positioned over the stylet 49 and the spring 72 is wound on the outer surface of the tube 70. At the distal end of the spacer tube 70, the diameter of the spring 72 is reduced at a step 78 to the diameter of the stylet 49. The winding of the spring 72 continues at this dimension to the distal end of the catheter 10.

The proximal end 46 of the balloon 45 is then stretched over this subassembly. Since it may be difficult to stretch the balloon 45 over the convolutions of the spring 72 at the step 78, it may be desirable to initially place the subassembly within the balloon support tube 74 and position the tube 74 so that it covers the distal end of the spacer tube 70. Then the proximal end 46 of the balloon 45 can be stretched over the distal end of the balloon support tube 74.

Once the balloon 45 has been mounted, the assembly can be disposed within the stress relief tube 76 which is positioned within the wall 62. In this embodiment of FIG. 4, the regions interior of the wall 61 and exterior of the spacer tube 70 can then be filled with a urethane adhesive to maintain these elements in their desired concentric relationship. The adhesive 83 should not contact the stylet 49 which is intended to move freely within the spacer tube 70 and the spring 72. The outer surface of the adhesive 83 can be tapered distally inwardly from the outer surface of the wall 61 to the distal end of the stress relief tube 76. This tapered adhesive as well as the tube 76 provide a gradually reduced diameter for the catheter 10 which aids in relieving bending stresses which may be encountered. With the adhesive 83 positioned as illustrated, the cavity 62 communicates through the spacer tube 70 with the regions interior of the tube 45.

A further embodiment of the invention, illustrated in FIG. 6, provides a narrower configuration for the hub 41. The elements illustrated in this embodiment which have characteristics similar to those previously discussed are designated with the same reference numerals followed by the lower case letter "a".

The embodiment of FIG. 6 is similar to that of FIG. 4 except that the stress relief tube 76a is not disposed within the outer wall 61a of the hub 41a. This permits the outer wall 61a to have a reduced diameter. The spacer tube 70 of the FIG. 4 embodiment is eliminated in this case and the spring 72a is wound over the stylet 49a without a change in diameter. In this embodiment, the balloon support tube 74a is also positioned outwardly of the spring 72a and adapted to receive the proximal end 46a of the spring 45a. The adhesive 83a is disposed outwardly of the spring 72a and the balloon support tube 74a, and inwardly of the wall 61a and the strain relief tube 76a.

Both of these embodiments of the catheter 10 can have a distal end such as that illustrated in FIG. 5. At the distal end it is important that the balloon 45 be provided with a fixed relationship with the stylet 49. This can be accomplished with the threads 52 which are tightly wound around the balloon 45 compressing the balloon against the spring 72. A cyanoacrylate adhesive 85, or other suitable bounding means, can be disposed between the spring 72 and the stylet 49 to achieve this fixed relationship. This adhesive 85 is preferably provided proximally of the distal end 47 of the balloon 45 leaving a cavity which can then be filled with a UV plug 87 of material, such as an activated urethane adhesive, which provides the catheter with a flexible distal tip 90.

In the foregoing embodiments, it is of particular importance that the spring 72 be disposed between the stylet 49 and the interior surface of the balloon 45. Since this balloon 45 is required to extend to as much as six times its normal length, it will tend to contract radially inwardly as it is axially extended. It has been found that in the absence of the spring or other means for separating the stylet 49 from the balloon 45, that the balloon will eventually grip the stylet and prevent any further distal movement of the stylet 49 or the balloon 45. With the spring 72 positioned between the balloon 45 and the stylet 49, the convolutions of the spring 72 tend to grip the radially contracting balloon 45 and aid in the extension of the balloon as these convolutions separate. Interiorly of the spring 72, the convolutions provide a surface which offers substantially no resistance to the axial movement of the stylet 49.

Figure 8:
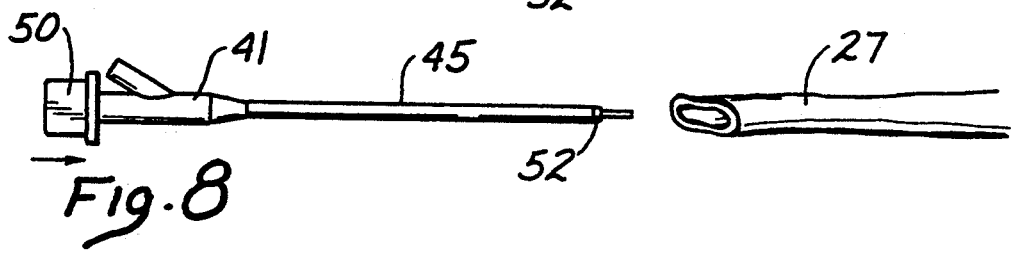

A method of the present invention is illustrated in FIGS. 7–13. As noted, when the internal mammary artery 27 is initially mobilized it tends to spasm and contract radially. It is this state which is to be overcome by stretching the artery 27. Initially the catheter 10 is positioned with the stylet 49 retracted and the balloon axially contracted and radially enlarged. From this normal state illustrated in FIG. 7, the Luer cap 50 can be moved in the direction of the hub 41 advancing the stylet 49 to move the distal tip 90 away from the hub 41. This stretches the balloon 45 to its axially extended, radially contracted state. The catheter 10 can be locked in this state by screwing the Luer cap 50 onto the inlet port 63 of the hub 41, as illustrated in FIG. 8.

Figure 9:
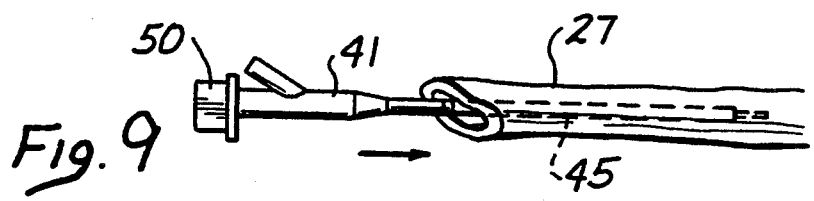
Figure 10:
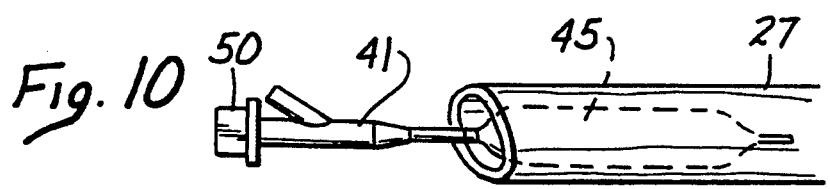
Figure 11:
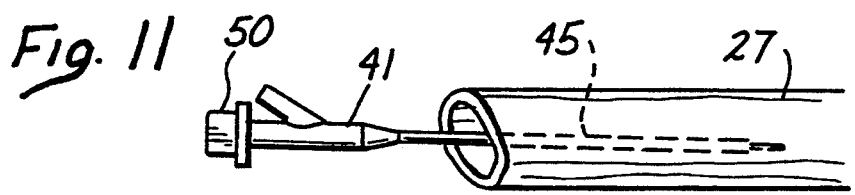
Figure 12:
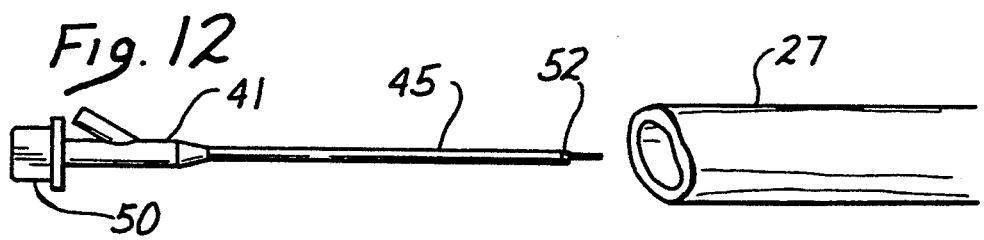

At this point, the catheter 10 is ready to be inserted into the artery 27 which is now in spasm as a result of mobilization, as shown in FIG. 9. When the catheter in the extended state is positioned within the artery 27, the balloon 45 can be inflated by introducing air or fluid into the side port 67. In this important step illustrated in FIG. 10, the balloon engages the artery 27 with a force which has only radial components. In other words, the balloon 45 moves radially outwardly opposing the spasm and stretching the artery 27 outwardly but not longitudinally. There is no axial movement of the catheter 10 and particularly the balloon 45 during this inflation step. As a result, the intima is merely pressed against the inner wall of the vessel 27 and is not subjected to any damaging shear stresses.

Figure 13:
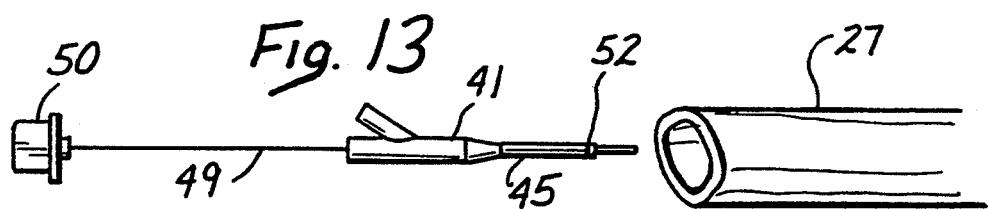

When the artery 27 has been expanded and the spasm has been relieved the balloon 45 can be deflated (FIG. 11) and the catheter 10 withdrawn axially (FIG. 12) from the arterial conduit 27. This will leave the artery 27 in a patent enlarged configuration ready for attachment to the associated coronary artery. As shown in FIG. 13, the Luer cap 50 can be unlocked from the hub 41 to permit the balloon 45 to return to its contracted state prior to disposal of the catheter 10.

A simplified embodiment of the invention is illustrated in FIG. 14. In this embodiment, elements similar to those previously discussed are designated with the same reference numerals followed by the lower case letter "b". This particular embodiment is simplified not only in its structure, which includes fewer elements, but also in its method of manufacture as well as its method of use.

As in the previous embodiments, the catheter 10b of FIG. 14 includes a hub 41b having a strain relief section 43b which engages a balloon support tube 74b. A stylet 49b extends through the support tube 74b with its proximal end fixed to the hub 41b. A soft tip 94, which can be formed from an elastomeric material or a spring, is configured to receive the distal end of the stylet 49b and to be adhered to the stylet 49b by a suitable adhesive.

In this embodiment, a balloon 45b is provided with a proximal end 46b which is attached to the balloon support tube 74b by windings 96. Similarly, a distal end 47b of the balloon 45b can be attached to the stylet 49b by windings 98. In a preferred embodiment both of the windings 96, 98 are formed with polyester thread. Other means of attachment, including adhesives, can also be used for this purpose.

Of particular importance to this embodiment is the fact that 10 the windings 96 and 98 are separated during manufacture by a distance such as six inches, which is sufficient to stretch the balloon to its elongated state. Thus, in this embodiment, the catheter 10b is manufactured with the balloon fully stretched so that it is provided to the surgeon in the general configuration illustrated in FIG. 8. With this embodiment, there is no need for the surgeon to move the stylet 49 into the hub 41 in order to stretch the balloon 45 as previously discussed with reference to FIG. 7.

In an embodiment of this type, it is important that the balloon 45b be formed from a material which is not deleteriously affected by sterilization. Some elastomeric materials in a stretched configuration lose their elasticity when they undergo sterilization. When such materials are desired for the balloon 45, the foregoing embodiments of FIGS. 4 and 6 may be preferred.

A material of particular interest for the balloon 45b in the embodiment of FIG. 14 is silicone. When the balloon 45b is manufactured from this material, it can be fully stretched to the elongated configuration illustrated in FIG. 8 during the manufacturing process. Sterilization of the balloon 45b in its stretched configuration will not affect the elasticity of the silicone. Thus the catheter 10a can be provided to the surgeon fully sterilized with the balloon 45b in its elongated configuration.

This choice of materials for the balloon 45b offers several significant advantages to the structure of the catheter 10b as well as its processes for manufacturing and use. For example, if the surgeon is not required to elongate the balloon as previously described with reference to FIG. 7, there is no need for a spring, such as the spring 72, which would normally separate the stylet 49 from the balloon 45. This of course enables the entire balloon structure as well as the balloon support tube 74b to be configured with a significantly reduced diameter. With the reduced diameters, strain relief associated with the section 43b can also be reduced in complexity. Therefore in the embodiment of FIG. 14, the strain relief tube 76 and spacer tube 70 of FIG. 4 can be eliminated.

In the manufacture of the catheter 10b, elongation of the balloon 45b can be achieved by moving the stylet 49b distally through the balloon thereby separating the windings 96 and 98 and stretching the balloon 45b. This step in the manufacturing process can be facilitated by pressurizing the balloon 45b in order to separate its walls from the stylet 49b. After the balloon 40b is stretched, the proximal end of the stylet 49 can be seated in a hole 100 in the hub 41b and permanently held in place by a suitable adhesive. It follows that in this simplified embodiment of FIG. 14, it is not necessary to provide the cap 50 (FIG. 1) at the proximal end of the stylet 49.

The configuration of the hub 41b can also be simplified in this embodiment. With the stylet 49b fixed within the hub 41b, the central channel of the hub 49b is free for use in inflating the balloon 45b. Thus a syringe 102 or other inflation means can be attached to the hub 41b in order to inflate the balloon 45b through a lumen 104 which extends axially through the hub 41b and the tube 74b.

The method for using the embodiment of FIG. 14 is simplified from the method previously disclosed with reference to FIGS. 7-13. This simplification results from the fact that the catheter 10a is provided to the surgeon with the balloon 45b in the elongate stretched configuration illustrated in FIG. 8. Thus the surgeon is not required to insert the stylet 49 or otherwise deploy the balloon 45 as previously discussed with reference to FIG. 7. The method for using the embodiment of FIG. 14 is similar to that previously disclosed with reference to FIGS. 8-12. However, the embodiment of FIG. 14 will typically be discarded in the state illustrated in FIG. 12, there being no apparatus available to the surgeon for returning the balloon 45 to a contracted state as previously discussed with reference to FIG. 13.

With the exceptions mentioned above the present invention is not material dependent. However, in a preferred embodiment of the concept, the strain relief tube 76 is formed from polyvinylchloride while the spacer tube 70 and the balloon support tube 74 are formed from a polyamide material. The adhesives 83 and 87 in this embodiment are UV activated urethanes while the adhesive 85 is preferably a cyanoacrylate. While these materials are preferred for some embodiments of the invention, any one of the foregoing elements can be formed from a different material all within the scope of the present invention.

It will also be apparent that various elements of the catheter 10 can be replaced with similar structure. For example, the spring 72 might be replaced by a tubular structure providing the necessary separation between the balloon 45 and the stylet 49. The balloon 45 could also be formed of any suitable material providing the desired elastomeric characteristics for the extended longitudinal expansion contemplated by the present invention.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A device for relieving spasm in a blood vessel, the device having a generally longitudinal configuration and extending between a proximal end and an opposing distal end, including:
   a hub disposed at the proximal end of the device and having portions defining a channel through the hub;
   an elongate spring extending from the hub to the distal end of the device and having a multiplicity of convolutions defining a passage through the spring;
   a stylet disposed to extend through the channel of the hub and the passage of the spring in sliding engagement with the portions of the hub and the convolutions of the spring;
   a balloon having an elongate configuration with a proximal end of the balloon in a fixed relationship and fluid communication with the hub, and a distal end of the balloon in a fixed relationship with the stylet in proximity to the distal end of the device; and
   means for advancing the stylet through the channel of the hub and the passage of the spring to stretch the balloon from an axially shortened, radially expanded state to an axially extended, radially contracted state.

2. The device recited in claim 1 wherein the balloon in its axially extended, radially contracted state is at least three times longer than the balloon in its axially compressed, radially expanded state.

3. The device recited in claim 2 wherein the balloon in its axially extended, radially compressed state is at least four times longer than the balloon in its axially compressed, axially extended state.

4. The device recited in claim 1 wherein the hub further comprises:
   a housing;

a balloon support tube having a proximal end disposed inwardly of the housing and a distal end disposed outwardly of the spring.

5. The device recited in claim 4 wherein the proximal end of the balloon extends over the balloon support tube.

6. The device recited in claim 4 wherein the hub further comprises:
a spacer tube disposed inwardly of the balloon support tube, inwardly of the spring, and outwardly of the stylet.

7. A device for relieving spasm in a blood vessel, the device having a generally longitudinal configuration and extending between a proximal end and an opposing distal end, including:
a hub disposed at the proximal end of the device and having portions defining a channel through the hub;
a stylet disposed to extend through the channel of the hub in sliding engagement with the portions of the hub;
a balloon having an elongate configuration with a proximal end of the balloon disposed in a fixed relationship with the hub, and a distal end of the balloon disposed in a fixed relationship with the stylet;
means for advancing the stylet through the channel of the hub to stretch the balloon from an axially shortened, radially expanded state, to an axially extended, radially contracted state;
means disposed between the balloon and the stylet for at least partially decreasing any frictional forces resulting from contact between the balloon and the stylet; wherein,
the means for decreasing frictional forces comprises an elongate spring extending from the hub of the distal end of the device.

8. A combination, comprising:
a blood vessel having walls defining a central conduit having a first patency when the vessel is in a normal state, the walls of the vessel being in spasm to provide the central conduit with a second patency less than the first patency when the vessel is in a spasmed state;
means for relieving the spasm in the walls to move the vessel from the spasmed state toward the normal state and thereby increase the patency of the vessel from the second patency toward the first patency;
a hub included in the relieving means;
a tube extending from the hub in the relieving means;
a stylet extending from the hub and through the tube in the relieving means;
an elongate balloon included in the relieving means and having a first end attached to the tube and a second end attached to the stylet, the balloon being longitudinally stretched along the stylet between the first end of the balloon and second end of the balloon to a length generally equal to about the length of the blood vessel; and
means for radially extending the balloon within the conduit of the vessel and for exerting a force generally exclusive of any sheer force components against the walls of the vessel in the spasmed state to relieve the spasm of the walls along substantially the entire length of the vessel by moving the vessel from the spasmed state toward the normal state and thereby increasing the patency of the vessel.

* * * * *

UNITED STATES PATENT AND TRADEMARK OFFICE
CERTIFICATE OF CORRECTION

PATENT NO. : 5,354,276
DATED : October 11, 1994
INVENTOR(S) : Fonger et al.

It is certified that error appears in the above-identified patent and that said Letters Patent is hereby corrected as shown below:

Col. 6, line 61 after the word "that" delete the numeral "10".

Signed and Sealed this

Seventh Day of March, 1995

*Attest:*

BRUCE LEHMAN

*Attesting Officer*    *Commissioner of Patents and Trademarks*